United States Patent [19]

Dalton

[11] Plant 4,021

[45] Mar. 8, 1977

[54] APPLE TREE

[76] Inventor: William E. Dalton, Rte. No. 2, Box 252, Hendersonville, N.C. 28739

[21] Appl. No.: 634,441

[22] Filed: Nov. 24, 1975

[51] Int. Cl.[2] ..... A01H 5/03
[52] U.S. Cl. ..... Plt./34
[58] Field of Search ..... Plt./34

*Primary Examiner*—Robert E. Bagwill
*Attorney, Agent, or Firm*—Robb & Robb

EXEMPLARY CLAIM

1. A new and distinct variety of apple tree, substantially as herein shown and described, characterized particularly as to novelty by a general resemblance in some respects to the variety "Golden Delicious" (unpatented), but being principally distinguished therefrom by a semi-dwarf habit of growth, with crotch angles of almost 90°; a more spreading spur type fruiting habit which enables better development and easier picking of the fruit; a larger and more uniform fruit size throughout the tree, with most of the fruit grading tray-pack or extra fancy; excellent russet resistance (at least 95% free of russetting) far superior to the normally heavy russetting of the variety "Golden Delicious;" an attractive golden yellow fruit color which has a distinctive and attractive reddish blush even at low altitudes; better hardiness than "Golden Delicious," with the ability to withstand lower temperatures during the blooming period; a more prolific fruit bearing habit than "Golden Delicious" when grown under the same climate and soil conditions; a longer harvest period usually ranging for about a full month, beginning in early September and continuing into early October at Hendersonville, N.C.; and a self-fertile habit, with a suitability for use as a pollinator for other varieties.

4 Drawing Figures

The present invention relates to a new and distinct variety of apple tree of unknown parentage, but which I believe to be a seedling of the apple variety known as "Golden Delicious" (unpatented). The seedling was discovered by me growing in a fence row on my farm property located at Hendersonville, N.C., where I have maintained for many years an orchard of apple trees. Out of curiosity, I carefully preserved the seedling in the fence row and allowed it to grow until I became convinced by my close observations thereof that it was apparently a new variety and different from all other varieties, including "Golden Delicious," which I was growing in my orchard aforesaid, or otherwise known to me.

After reaching this conclusion, I began propagating the new seedling on my regular orchard grounds, as performed by me by grafting, and continued to keep the original seedling tree and its progeny under close observations through four generations. These observations have conclusively proved to me that the progeny come true to the original tree, and that the new seedling constitutes a new and improved apple tree variety which is endowed with a unique combination of characteristics having superior commercial value and which distinguish the same from all other apple tree varieties, particularly including "Golden Delicious," as evidenced by the following principal features which are outstanding therein:

1. A semi-dwarf habit of growth, with crotch angles of almost 90°;

2. A more spreading spur type fruiting habit which enables better development and easier picking of the fruit;

3. A larger and more uniform fruit size throughout the tree, with most of the fruit grading tray-pack or extra fancy;

4. Excellent russet resistance (at least 95% free of russetting) far superior to the normally heavy russetting of the variety "Golden Delicious;"

5. An attractive fruit color which has a distinctive and attractive red blush even at low altitudes;

6. Better hardiness than "Golden Delicious," with the ability to withstand lower temperatures during the blooming period;

7. A more prolific fruit bearing habit than "Golden Delicious' when grown under the same climate and soil conditions;

8. A longer harvest period usually ranging for about a full month, beginning in early September and continuing into early October at Hendersonville, N.C.; and 9. A self-fertile habit, with a suitability for use as a pollinator for other varieties.

The accompanying drawings show the growth habit and typical specimens of the foliage and fruit of my new variety as depicted in color as nearly true as it is reasonably possible to make the same in a color illustration of this character, said fruit being shown in both elevation and in cross-section, and the foliage specimens depicting both the upper and under surfaces of typical leaves.

The following is a detailed description of the new variety, with color terminology in accordance with Maerz and Paul Dictionary of Color, except where general color terms of ordinary dictionary significance are obvious.

Locality where grown and observed: Hendersonville, N.C.

Dates of first and last pickings: Usually about September 7 and October 7, respectively, at Hendersonville.

Tree: Semi-dwarf (medium size); vigorous; low spreading; vase formed; rapid growing; hardy; very productive; regular bearer.

*Trunk.*—Stocky; medium smoothness.

*Branches.*—Medium thickness; medium smoothness; much-branched. Color — Brown. Lenticles — Medium number; medium size.

*Leaves.*—Medium size; ovate; taper-pointed; medium thickness; smooth. Length — Long (about 3¼ inches). Width — Medium (about 2 inches).

Color — Dark green on upper surface and lighter green on under surface. Margin — Crenate; finely serrate. Petiole — Medium length (about 1 inch); medium thickness.

Flowers: Medium early; medium size.

*Dates of first and full bloom.*—About April 20 and April 25, respectively.

*Color.*—Pink, Plate 42; B-1.

Fruit:

*Maturity when described.*—Eating hard; about September 15.

*Size.*—Uniform. Axial diameter — From about 2¾ inches to 3½ inches. Traverse — About 3⅛ inches.

*Form.*—Uniform; regular; oblong; angular.

*Cavity.*—Symmetrical; flaring toward apex; lipped. Depth — About ⅝ inch. Breadth — About 1⅜ inches.

*Basin.*—Rounded; wide base.

*Stem.*—Stout. Length — About 1 inch. Bracts — Present; from 1 to 3 in number.

*Calyx.*—Closed; about ⅜ inch long; erect. Outer surface — Pubescent. Inner surface — Glabrous.

*Eye.*—Medium size.

*Skin.*—Thick; smooth; glossy; waxed. Dots — Conspicuous; few in number; small; submerged. Color — Light brown, Plate 6, C-2. Distribution — Even. Ground color — Light orange with almost red blush, Plate 11, G-2. Color markings — Blushed. Color — Heather, Plate 45, J-1. Bloom — Scant. Scarfskin — Light; uniformly distributed. Color — White. General color effect — Golden yellow overlaid with reddish blush.

*Flesh.*—Juicy. Color — White, with yellowish tint. Texture — Firm; crisp. Flavor — Delicate. Aroma — Pronounced. Quality — Best. Core — Median. Bundle area — Medium size; cordate; acute at base in bundle. Halves of core area — Equal. Bundles — Conspicuous; in one whorl. Alternate bundle — Reaches tube below stamens. Core lines — Clasping; distinct in cross section. Carpellary area — Distinct; large. Calyx tube — Pubescent; funnel form. Stem of funnel — Short. Depth of tube to shoulder — About ⅝ inch. Entire depth — About ¾ inch. Styles — Present; united. Stamens — In whorls. Axillary cavity — Present. Seed cells — Open. Cell walls — Thick. Length — About ½ inch. Breadth —About ¼ inch. Longitudinal section — Narrowly ovate. Cross section — Narrow.

Seeds: Usually 10 and all perfect; usually 2 per cell.

*Length.*—About ⅜ inch.

*Breadth.*—About ¼ inch.

*Form.*—Acuminate.

*Color.*—Montella, Plate 8, J-11.

Use: Market; local; dessert; culinary.

Keeping quality: Good; about 90 days in ordinary storage.

Insect and disease resistance: Medium resistance to usual apple insects and diseases, as determined by comparison with other varieties grown under the same conditions at Hendersonville, N.C.

General observations: In comparison with the variety known as "Magnolia Gold" (U.S. Plant Pat. No. 3,110), my new variety is genetically semi-dwarf in its habit of growth, while "Magnolia Gold" is not; and although the new variety bears fruit as heavily as "Magnolia Gold," the fruit of the new variety is far superior in size when grown under the same conditions.

I claim:

1. A new and distinct variety of apple tree, substantially as herein shown and described, characterized particularly as to novelty by a general resemblance in some respects to the variety "Golden Delicious" (unpatented), but being principally distinguished therefrom by a semi-dwarf habit of growth, with crotch angles of almost 90°; a more spreading spur type fruiting habit which enables better development and easier picking of the fruit; a larger and more uniform fruit size throughout the tree, with most of the fruit grading tray-pack or extra fancy; excellent russet resistance (at least 95% free of russetting) far superior to the normally heavy russetting of the variety "Golden Delicious;" an attractive golden yellow fruit color which has a distinctive and attractive reddish blush even at low altitudes; better hardiness than "Golden Delicious," with the ability to withstand lower temperatures during the blooming period; a more prolific fruit bearing habit than "Golden Delicious" when grown under the same climate and soil conditions; a longer harvest period usually ranging for about a full month, beginning in early September and continuing into early October at Hendersonville, N.C.; and a self-fertile habit, with a suitability for use as a pollinator for other varieties.

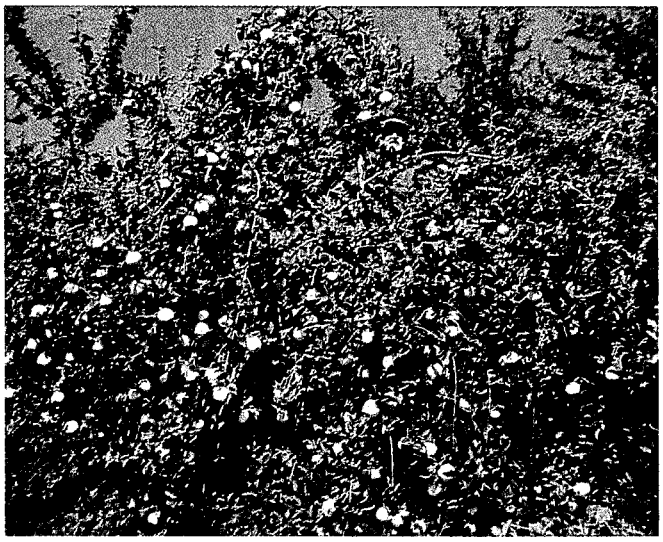
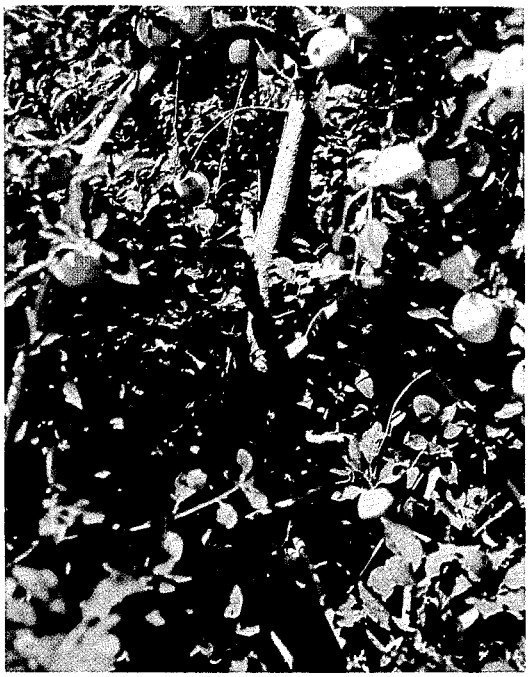
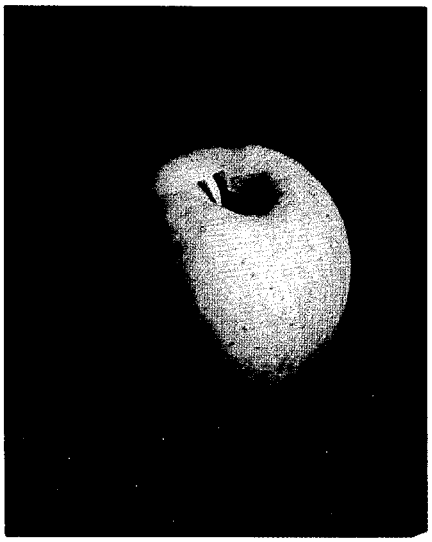

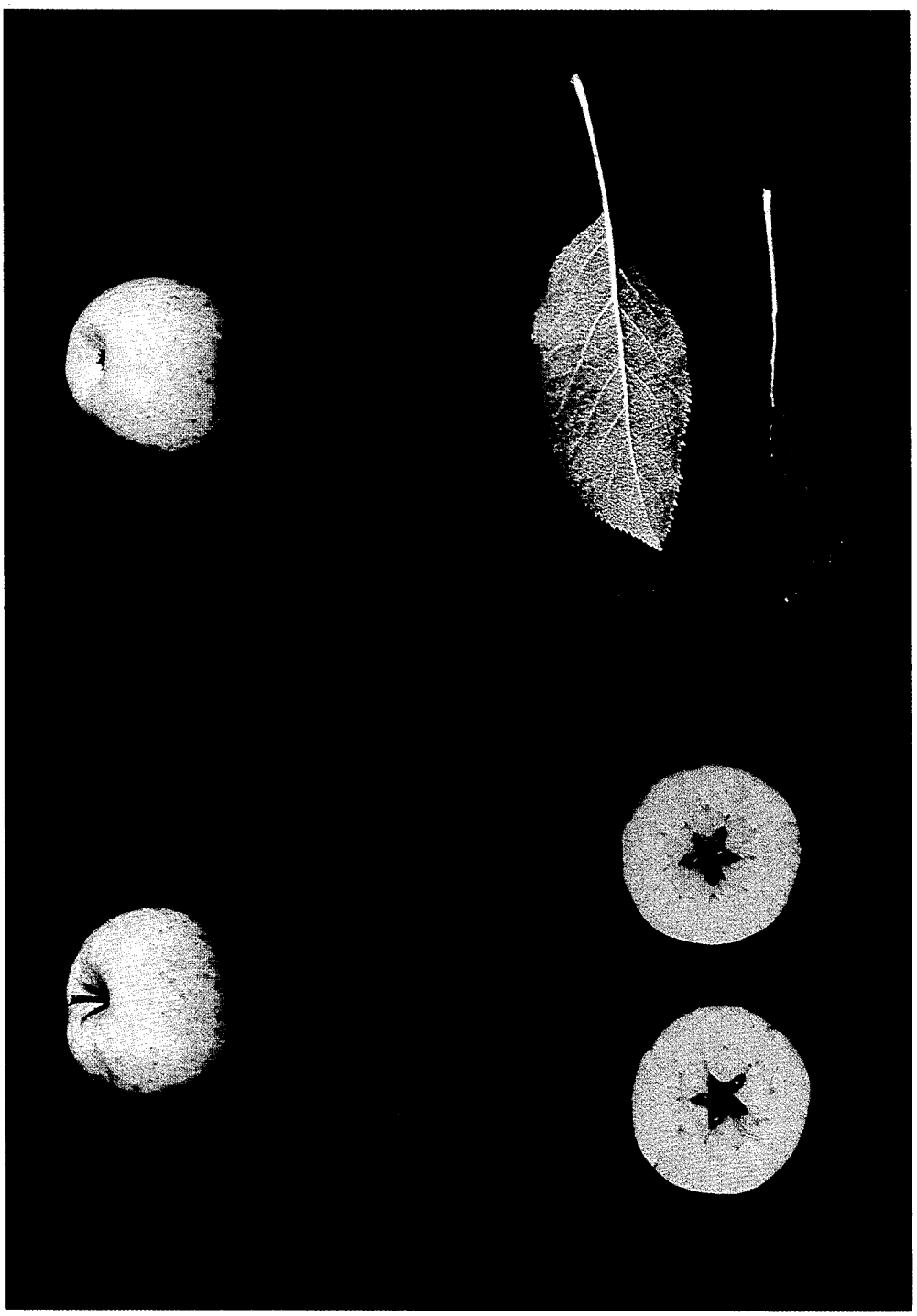

* * * * *